United States Patent
Wang et al.

(10) Patent No.: US 9,452,174 B2
(45) Date of Patent: *Sep. 27, 2016

(54) ORAL TRANSMUCOSAL PHARMACEUTICAL COMPOSITIONS INCLUDING TESTOSTERONE AND A C-SERM

(71) Applicant: Professional Compounding Centers of America (PCCA), Houston, TX (US)

(72) Inventors: Tsu-I Catherine Wang, Sugar Land, TX (US); Bruce Vincent Biundo, Houston, TX (US)

(73) Assignee: Professional Compounding Centers of America, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/799,389

(22) Filed: Jul. 14, 2015

(65) Prior Publication Data

US 2016/0051564 A1    Feb. 25, 2016

Related U.S. Application Data

(60) Provisional application No. 62/039,817, filed on Aug. 20, 2014.

(51) Int. Cl.
| | |
|---|---|
| *A01N 45/00* | (2006.01) |
| *A61K 31/56* | (2006.01) |
| *A61K 31/568* | (2006.01) |
| *A61K 31/138* | (2006.01) |
| *A61K 47/20* | (2006.01) |
| *A61K 9/20* | (2006.01) |
| *A61K 9/00* | (2006.01) |

(52) U.S. Cl.
CPC ............. *A61K 31/568* (2013.01); *A61K 9/006* (2013.01); *A61K 9/0056* (2013.01); *A61K 9/2013* (2013.01); *A61K 31/138* (2013.01); *A61K 47/20* (2013.01)

(58) Field of Classification Search
None
See application file for complete search history.

(56) References Cited

U.S. PATENT DOCUMENTS

| | | |
|---|---|---|
| 5,460,820 A | 10/1995 | Ebert et al. |
| 2008/0015170 A1 | 1/2008 | Buch et al. |
| 2010/0256129 A1 | 10/2010 | Zhi |
| 2015/0065426 A1 | 3/2015 | Wang et al. |

FOREIGN PATENT DOCUMENTS

WO    00/74684 A1    12/2000

OTHER PUBLICATIONS

PCT/US2015/045917, Nov. 24, 2015, Professional Compounding Centers of America, International Search Report and Written Opinion of ISA.

*Primary Examiner* — Jeffrey H Murray
(74) *Attorney, Agent, or Firm* — David G. Woodral; Fellers, Snider, Blankenship, Bailey & Tippens, P.C.

(57) ABSTRACT

Formulations for oral transmucosal compositions including a synergistic combination of low doses of testosterone with a clomiphene-like selective estrogen receptor modulator (C-SERM) that are combined with transmucosal absorption enhancers are disclosed. Oral transmucosal compositions can be for fast release or slow release, and can be administered to increase bloodstream testosterone levels and thereby reduce symptoms of testosterone deficiency. Oral transmucosal compositions include liquid dosage forms, solid dosage forms, and chewing gums. Further dosage forms include mucoadhesive thin strips, thin films, tablets, patches, and tapes, among others. Other dosage forms are: mucoadhesive liquids such as gel-forming liquids; gel-forming semisolids; and gel-forming powders, among other dosage forms that exhibit mucoadhesive properties, and provide oral transmucosal delivery of testosterone and C-SERM. Oral transmucosal compositions will deliver testosterone and C-SERM directly into the patient's bloodstream, and provide high bioavailability of testosterone and C-SERM; therefore, the required doses are lower.

10 Claims, No Drawings

ORAL TRANSMUCOSAL PHARMACEUTICAL COMPOSITIONS INCLUDING TESTOSTERONE AND A C-SERM

CROSS-REFERENCE TO RELATED APPLICATIONS

This application claims priority to U.S. Provisional Application Ser. No. 62/039,817, filed Aug. 20, 2014, which is hereby incorporated by reference.

BACKGROUND

1. Field of the Disclosure

The present disclosure relates generally to pharmaceutical compositions, and more particularly, to oral transmucosal pharmaceutical compositions including testosterone synergistically combined with a clomiphene-like selective estrogen receptor modulator (C-SERM) for maintaining pituitary gonadotropins within normal physiologic levels.

2. Background Information

Male testosterone deficiency is a syndrome associated with hormonal profile changes that negatively affect libido, sexual function, mood, behavior, lean body mass, and bone density. Further, testosterone deficiency has been shown to be related to low quality of erections, loss of libido, osteoporosis, weight gain, muscle weakness, decreased lean body mass, diabetes mellitus, and cognitive changes. The decrease in serum testosterone levels may be due to primary testicular failure and/or dysfunction of the hypothalamic-pituitary axis. This testosterone deficiency in aging males is associated with increased body weight and adipose tissue, and changes in estrogen levels due to peripheral conversion of testosterone to estradiol. The negative feedback mechanism from excess estradiol results in a paradoxically low luteinizing hormone (LH) secretion from the pituitary despite a physiologically low testosterone level. Unfortunately, low LH secretion results in a decrease in testosterone production.

Currently, the most common treatment for symptomatic male testosterone deficiency is testosterone therapy employing various transdermal (e.g., implanted pellets, patches, gels, etc.), oral, buccal, and injectable delivery methods. These methods typically involve very high doses of testosterone. The main purpose of the testosterone replacement therapy is to achieve a normal range of testosterone serum levels.

Oral therapy of testosterone lacks effectiveness because testosterone is metabolized extensively during the first passage of the liver before reaching the systemic blood circulation (e.g., the first-pass effect). Intramuscular injections of testosterone esters are widely used, but severe drawbacks for this form of treatment include local pain, tolerability, and the unphysiologically high levels of testosterone in the body during the first days/weeks after injection. Local pain is attributed to the large volumes of testosterone injected at a specific injection site. Other drawbacks to intramuscular injections include the need for required assistance of health care professionals thereby making injections inconvenient and expensive. These same drawbacks also apply to some of the transdermal applications, such as, for example implanted pellets.

Transdermal administration (e.g., implanted pellets, patches, gels, etc.) possesses the benefits of the avoidance of the first-pass effect as well as the elimination of local pain at the injection site. Unfortunately, transdermal compositions, excluding implanted pellets, currently prescribed for hypogonadal men include from 40 mg to 120 mg daily doses of which only a low percentage is absorbed through the skin. Another drawback is that a large part of the testosterone remains on the skin with the potential risk of being transferred to another person through direct skin-to-skin contact. Additionally, the non-absorbed portion of testosterone is lost to the surrounding environment making these formulations non-environmentally-friendly. Another common side effect of transdermal compositions is local skin irritation, which is likely due to the very high ethanol content of such formulations.

Oral transmucosal delivery is a particularly advantageous delivery route because it is a non-invasive drug delivery method. Oral transmucosal delivery promotes better patient compliance and involves lower costs than invasive procedures such as injection and implantation of pellets. Oral transmucosal delivery also results in a much shorter onset time (e.g., the time from administration to therapeutic effect) than oral delivery and may be easily self-administered. Oral transmucosal administration involves the patient holding the composition within the oral cavity (e.g., between the cheek and gum, beneath the tongue, etc.) while the API dissolves in the available fluid (e.g., saliva), diffuses through the mucosa lining of the mouth, and enters the bloodstream bypassing the gastrointestinal tract as well as hepatic metabolism.

Selective Estrogen Receptor Modulators (SERMs) are structurally unique compounds that interact with intracellular estrogen receptors in target organs. SERMs can possess either antagonist or agonist properties, and in certain cases, may possess both properties. Some SERMs, such as, tamoxifen and raloxifene possess estrogen agonist properties that cause unusual pharmacological effects to be exhibited when these particular SERMs interact with certain tissues (e.g., bone, liver and cardiovascular system tissues). Additionally, these same SERMs possess estrogen antagonist properties when these particular SERMs interact with other tissues (e.g., brain and breast tissues). Finally, these same SERMs possess mixed agonist/antagonist properties when interacting with uterine tissue. Clomiphene and SERMs that mimic clomiphene, act specifically as an estrogen antagonist in the brain, specifically in the hypothalamus and pituitary sites.

Within the testosterone negative feedback mechanism, estradiol received at hypothalamus receptor sites slows down the release of GnRH from the hypothalamus which in turn results in the reduction of LH/FSH production by the pituitary gland. Estradiol received at the pituitary gland also results in the reduction of LH/FSH production by the pituitary gland. Clomiphene acts to increase the production and release of GnRH by the hypothalamus as well as production and release of LH and FSH from the pituitary gland. LH and FSH then act on the testes to increase the production of testosterone and sperm, respectively. Therefore, clomiphene-like SERMs can be used for both hypogonadism and male infertility.

SUMMARY

The present disclosure refers to oral transmucosal compositions that include a synergistic combination of low doses of testosterone with a clomiphene-like selective estrogen receptor modulator (C-SERM) in order to increase testosterone levels in a patient's bloodstream and reduce symptoms of testosterone deficiency. The synergistic combination of low doses of testosterone and C-SERM may lead to increased levels of testosterone in the patient without the side effect of pituitary suppression of LH and FSH secretion. As such, oral transmucosal compositions can be used in treating a wide variety of conditions resulting from testosterone deficiency in men.

According to some embodiments, APIs include low doses of testosterone synergistically combined with a C-SERM, such as clomiphene (Clomid®), analogs thereof, or any other chemical compound that acts on estrogen receptors and blocks the normal estrogen feedback control on the hypothalamus and subsequent negative feedback control on the pituitary.

In some embodiments, the C-SERM employed in oral transmucosal compositions is clomiphene. In these embodiments, clomiphene within oral transmucosal compositions is implemented as clomiphene citrate or an analog thereof. In other embodiments, clomiphene implemented within oral transmucosal compositions is zuclomiphene, enclomiphene, or a combination of these two clomiphene isomers.

In other embodiments, testosterone can be administered in the form of a testosterone ester. Examples of testosterone esters include testosterone cypionate, testosterone propionate, testosterone enanthate, testosterone heptylate, testosterone caproate, testosterone phenylpropionate, testosterone isocaproate, testosterone decanoate, testosterone acetate, testosterone laurate, or a pharmaceutically acceptable ester thereof, or any combination thereof.

In some embodiments, various additives are included to facilitate the preparation of suitable dosage forms. For example, additives include solvents, diluents, binders, disintegrants, lubricants, glidants, mucoadhesive polymers, thickening agents, transmucosal absorption enhancers, polymer plasticizers, pH adjusters, preservatives, sweeteners, flavors, colors, effervescent agents, stabilizing agents, antioxidants, and surfactants, among others.

In some embodiments, transmucosal absorption enhancers provide more efficient penetration of APIs through oral mucosal tissue. In these embodiments, the transmucosal absorption enhancers allow lower APIs dosage requirements.

In some embodiments, the amount of absorption enhancers included in oral transmucosal compositions range from about 0.1% to about 20%; with the most suitable amount being about 1% to about 10%. These percent ranges may refer to % weight by weight, % weight by volume, or % volume by volume.

In some embodiments, oral transmucosal compositions allow the delivery of testosterone and C-SERM directly into the patient's bloodstream bypassing the gastrointestinal tract and the hepatic metabolism. In these embodiments, oral transmucosal compositions will provide higher percentages of bioavailability of testosterone and C-SERM to the patient, and this also allows lower dosage requirements of testosterone.

In some embodiments, oral transmucosal compositions are administered in the oral cavity at the sublingual, palatal, buccal, gingival, or the like.

In some embodiments, oral transmucosal compositions may be tailored for individual patients according to clinical symptoms and baseline serum concentrations of testosterone and estradiol. These oral transmucosal compositions may be prescribed with various concentrations of testosterone and C-SERM, and suitable dosage regimens to more closely mimic the circadian rhythm and physiological pulsatile secretion of testosterone, thereby keeping the testosterone and estradiol levels within physiologic range.

In an example, oral transmucosal compositions are administered within a dosage range from about 25 mg/day to about 100 mg/day of testosterone, preferably from about 25 mg/day to about 50 mg/day; and from about 5 mg/day to about 100 mg/day of clomiphene, preferably from about 25 mg/day to about 50 mg/day.

According to some embodiments, oral transmucosal compositions include different components, such as active pharmaceutical ingredients (APIs), transmucosal absorption enhancers, suitable vehicles, and suitable additives, among others.

In some embodiments, oral transmucosal compositions include liquid dosage forms such as sublingual solutions, emulsions, suspensions, and liquid sprays, among others. In other embodiments, oral transmucosal compositions include solid dosage forms such as sublingual tablets, and buccal troches, among others. In yet other embodiments, oral transmucosal dosage forms include chewing gums.

In some embodiments, oral transmucosal dosage forms include mucoadhesive polymers as part of the compositions. Examples of dosage forms include mucoadhesive thin strips, thin films, tablets, patches, and tapes, among others. In other embodiments, dosage forms include: mucoadhesive liquids such as gel-forming liquid; semisolids such as gels, gel-forming ointments, and gel-forming pastes; gel-forming powders, or any other dosage forms that exhibit mucoadhesive properties and provide oral transmucosal delivery of testosterone and C-SERM.

In some embodiments, low dose APIs in any of the above identified dosage forms may result in acceptable testosterone levels in the patient. This contrasts with current popular topical treatment options which use very high dosages of testosterone to get a few milligrams of testosterone absorbed into the bloodstream.

In some embodiments, oral transmucosal dosage forms are designed for fast release and transmucosal absorption of testosterone and C-SERMs. In other embodiments, oral transmucosal dosage forms are designed for slow release and absorption of testosterone and C-SERMs over a prolonged period of time.

Numerous other aspects, features, and benefits of the present disclosure may be made apparent from the following detailed description.

DETAILED DESCRIPTION

The present disclosure is described here in detail. Other embodiments may be used and/or other changes may be made without departing from the spirit or scope of the present disclosure. The described embodiments are not meant to limit the subject matter presented here.

Definitions

As used here, the following terms have the following definitions:

"Active Pharmaceutical Ingredients (APIs)" refer to chemical compounds that induce a desired effect, and include agents that are therapeutically or prophylactically effective.

"Absorption Enhancer" or, equivalently, "Penetration Enhancer" refers to a substance used to increase the rate of permeation through the mucous membrane, skin or other body tissue of one or more substances (e.g., APIs) in a formulation.

"Clomiphene-like SERMs (C-SERMs)" refer to chemical compounds that act like clomiphene, as selective estrogen antagonist in the brain, specifically in the hypothalamus and pituitary sites. As such, the C-SERMs act to increase the release of GnRH, LH, and FSH. LH and FSH then act on the testes to increase the production of testosterone and sperm, respectively.

"Selective Estrogen Receptor Modulators (SERMs)" refer to chemical compounds that interact with intracellular estrogen receptors in target organs.

"Treating" and "Treatment" refers to reduction in severity and/or frequency of symptoms, elimination of symptoms and/or underlying cause, prevention of the occurrence of symptoms and/or their underlying cause, and improvement or remediation of damage.

"Vehicle" refers to a substance of no therapeutic value that is used to convey at least one API for administration.

Description of the Disclosure

The present disclosure is directed towards oral transmucosal compositions that include synergistic combinations of low doses of testosterone and C-SERM as APIs. These oral transmucosal compositions are proposed to increase testosterone levels, maintain pituitary gonadotropins within physiologic levels, and reduce symptoms of testosterone deficiency in men without the side effect of pituitary suppression of LH and FSH secretion.

As described previously, testosterone is peripherally converted to estradiol which serves as a major mediator of sex steroid-gonadotropin feedback. Thus, the secretion of LH and FSH are, to a large extent, modified by C-SERMs that affect the activity of estradiol. C-SERMs possess the capacity to blunt the activity of estradiol by competing with estradiol for the estrogen receptors of the hypothalamus and pituitary gland thereby increasing the amount of LH and FSH the body produces. These increased levels of LH and FSH correspond with increased production of testosterone and sperm, respectively. Therefore, C-SERMs can be used for both hypogonadism and male infertility.

Formulation

In some embodiments, oral transmucosal compositions include a synergistic combination of C-SERM and low doses of testosterone as APIs, transmucosal absorption enhancers, vehicles, and additives, among other suitable ingredients. In these embodiments, APIs include low doses of testosterone synergistically combined with a C-SERM, such as, clomiphene (Clomid®), analogs thereof, or any other chemical compound that acts on estrogen receptors to block the normal estrogen feedback control of the hypothalamus and subsequent negative feedback control of the pituitary gland.

In some embodiments, the C-SERM employed in oral transmucosal compositions is clomiphene. In these embodiments, clomiphene within oral transmucosal compositions is implemented as clomiphene citrate or an analog thereof. In other embodiments, clomiphene implemented within oral transmucosal compositions is zuclomiphene, enclomiphene, or a combination of these two clomiphene isomers.

In some embodiments, testosterone can be administered in the form of a testosterone ester. Examples of testosterone esters include testosterone cypionate, testosterone propionate, testosterone enanthate, testosterone heptylate, testosterone caproate, testosterone phenylpropionate, testosterone isocaproate, testosterone decanoate, testosterone acetate, testosterone laurate, or a pharmaceutically acceptable ester thereof, or any combination thereof.

In some embodiments, the synergistic effect of the C-SERM and low doses of testosterone lead to increased levels of testosterone and testosterone production in the patient without the side effect of pituitary suppression of LH and FSH secretion. Therefore, oral transmucosal compositions can be used in treating a wide variety of conditions resulting from testosterone deficiency in men.

In some embodiments, various additives are included to facilitate the preparation of suitable dosage forms. For example, additives include solvents, diluents, binders, disintegrants, lubricants, glidants, mucoadhesive polymers, thickening agents, transmucosal absorption enhancers, polymer plasticizers, pH adjusters, preservatives, sweeteners, flavors, colors, effervescent agents, stabilizing agents, antioxidants, and surfactants, among others.

In some embodiments, diluents for solid dosage forms include calcium carbonate, dibasic calcium phosphate, tribasic calcium phosphate, calcium sulfate, kaolin, microcrystalline cellulose, and other cellulose derivates, sodium chloride, starch and starch derivates, sucrose, dextrose, lactose, and sorbitol, among others.

Binders for solid dosage forms include starch and starch derivatives, gelatin, sucrose, glucose, dextrose, molasses, lactose, natural and synthetic gums, acacia, sodium alginate, extract of Irish Moss, panwar gum, ghatti gum, mucilage of isapol husks, carboxymethylcellulose, methylcellulose, cellulose derivatives, veegum, polyvinylpyrolidone, and polyethylene glycols, among others.

Disintegrants for solid dosage forms include veegum, agar, bentonite, alginic acid and alginic acid derivatives, guar gum, starch, sodium starch glycolate, other starch derivatives, clays, cellulose, and cellulose derivatives, among others.

Lubricants for solid dosage forms include stearic acid, stearic acid derivatives, stearic acid salts such as magnesium stearate and calcium stearate, talc, hydrogenated vegetables oils, polyethylene glycols, surfactants, and waxes, among others.

Additionally, solid dosage forms of oral transmucosal compositions include: a glidant, such as, colloidal silicon dioxide and talc, among others; a sweetening agent, such as, sucrose or saccharin, among others; natural or artificial flavors, such as, for example peppermint, methyl salicylate, or orange flavor, among others.

The pH adjusting agents include sodium bicarbonate, magnesium hydroxide, calcium carbonate, dibasic calcium phosphate, tribasic calcium phosphate, sodium bicarbonate, magnesium hydroxide, potassium hydroxide, citric acid, lactic acid, hydrochloric acid, sulfuric acid, phosphoric acid, sodium phosphate monobasic, and sodium phosphate dibasic, among others.

Surfactants include: polysorbates, such as, polysorbate 20, 40, 60, and 80, among others; sorbitan esters, such as, for example sorbitan monolaurate, sorbitan monopalmitate, sorbitan monooleate, among others; and sodium lauryl sulfate, among others.

Effervescent agents are usually a combination of one or more acids with one or more bases. Acids are selected from citric acid, tartaric acid, and the like. Bases can be sodium bicarbonate or other suitable agents that may react with acids, and produce gas.

In some embodiments, a stabilizing agent is used to stabilize the API for a specific dosage form. In these embodiments, the stabilizing agent used will depend on the API used as well as the other additive ingredients. Any suitable chemical substance may be used as a stabilizing agent. Stabilizing agents are known to those skilled in the art and therefore will not be discussed further herein.

Mucoadhesive polymers include: gums, such as, for example acacia, agarose, alginic acid, sodium alginate and other alginic acid derivatives, carrageenan, gelatin, gellan, guar gum, hakea gum, karaya gum, and locust bean gum, among others; chitosan and chitosan derivatives; hyaluronic acid, pectin, and other polysaccharides; gelatin, polyisoprene, polyisobutylene, polyetherurethane, polyvinylalcohol, polyvinylpyrrolidone, polycarbophil, polyethylene oxide polymers, and pullulan, among others. Mucoadhesive polymers also include cellulose derivatives such as ethyl cellulose, cellulose acetate, hydroxyethyl cellulose, hydroxypropylcellulose, hydroxypropylmethylcellulose, methylcellulose, methylhydroxyethylcellulose, and sodium carboxymethyl cellulose, among others; poly(acrylic acid)-based polymers such as polyacrylates, poly (methylvinylether-co-methacrylic acid), poly(acrylic acid-co-ethylhexylacrylate), poly(acrylic acid-co-acrylamide), poly(acrylic acid-co-butylacrylate), poly(acrylic acid-co-methyl methacrylate), poly (2-hydroxyethyl methacrylate), polymethacrylates, poly(alkylcyanoacrylate) and other cyanoacrylates, poly (isohexycyanoacrylate), poly (isobutylcyanoacrylate), and hydroxyethyl methacrylate, and any other polymer known to a person skilled in the art that exhibits mucoadhesive characters.

Plasticizers for mucoadhesive polymeric dosage forms include pullulan, hydroxypropyl methylcellulose, propylene glycol, glycerol, sorbitol, mannitol, polyethylene glycols (PEG 200, 400, 600, 1000, 1500, 2000), tartaric acid, malic acid, lactic acid, citric acid, and yonkenafil, and any other chemical known to a person skilled in the art that can increase the plasticity of any mucoadhesive polymer.

Bases for chewing gum include cellulosic polymer, and acrylic polymer, among others.

In some embodiments, transmucosal absorption enhancers provide more efficient penetration of APIs through oral mucosal tissue. In these embodiments, the transmucosal absorption enhancers allow lower APIs dosage requirements.

Oral transmucosal absorption enhancers include: enzyme inhibitors, such as, aprotinin and puromycin, among others; chitosan and chitosan derivatives such as chitosan glutamate, trimethyl chitosan, chitosan-4-thioglycolic acid, 5-methyl-pyrrolidine chitosan, and chitosan-4-thio-butyl-amidine, among others; alpha, beta, and gama cyclodextrins, such as, for example dimethyl cyclodextrin, sulfobutyl cyclodextrin, 2-hydroxypropyl-beta-cyclodextrin, polybeta-cyclodextin, and methylated beta-cyclodextrin, among others; bile salts, such as, for example sodium deoxycholate, sodium glycocholate, sodium glycodeoxycholate, sodium glycodihydrofusidate, sodium taurocholate, sodium taurodeoxycholate, sodium tauroglycocholate, sodium taurodihydrofusidate, and sodium ursocholate, among others; chelating agents, such as, for example sodium EDTA, citric acid, sodium citrate, sodium salicylate, methylsalicylate, methoxysalicylate, and polyacrylates, among others; alcohols, such as, ethanol and isopropanol, among others; fatty acids and derivatives, such as, for example oleic acid, methyloleate, capric acid, neodecanoic acid, elaidic acid, lauric acid, palmitoylearnitine, cod liver oil extract, mono glycerides and diglycerides of oleic acid and capric acid, lauric acid, sodium laurate, linoleic acid, sodium fusidate, sodium caprate, lyceryl monolaurate, glyceryl monooleate, glyceryl monostearate, sucrose fatty acid esters, and diethylene glycol monoethyl ether, among others; lecithins and phospholipids, such as, for example phodphatidylcholine, lysophosphatidyl choline, and didecanoylphophatidylcholine, among others; sulfoxides, such as, dimethylsulfoxide and decylmethyl sulfoxide, among others; polyols, such as, for example glycerin, propylene glycol, propanediol, and polyethylene glycols of various molecular weights, among others; urea and derivatives, such as, unsaturated cyclic urea, among others; surfactants, such as, for example sodium dodecyl sulfate, sodium lauryl sulfate, dioctyl sodium sulfosuccinate, nonylphenoxypolyoxyethylene, polyoxyethylene alkyl ethers, polyoxyethylene-9-lauryl ether, polyoxyethylene 23 lauryl ether, polyoxyethylene-20-cetyl ether, polyethyleneglycol dodecyl ether, polyethylene glycol-8 laurate, glyceryl monolaurate, polyoxyethylene stearates, polysorbates, sorbitan fatty acid esters, polyoxyethylene castor oil derivatives, benzalkonium chloride, cetylpyridinium chloride, and cetyltrimethylammonium bromide, among others. Other oral transmucosal absorption enhancers include alkylglycosides, azone, hyaluronic acid, sodium Hyaluronate, glycine chenodeoxycholate, lauroyl macroglycerides, isopropyl myristate, isopropyl palmitate, glutathione, witepsol, menthol, capsaicin, taurine, tocopheryl acetate, lauroyl macroglycerides, lionoleoyl polyoxyl-6 glycerides; diethylene glycol monoethyl ether, dextran sulfate, various saponins, poly-l-arginine, and l-lysine, and any other chemical known to a person skilled in the art that exhibits penetration enhancing effect on transmucosal absorption.

In some embodiments, the amount of absorption enhancers included in oral transmucosal compositions range from about 0.1% to about 20%; with the most suitable amount being about 1% to about 10%. These percent ranges may refer to % weight by weight, % weight by volume, or % volume by volume.

In some embodiments, oral transmucosal compositions include pharmaceutical solvents to produce sprays, solutions, emulsions, suspensions, gels, gel-forming liquids, ointments and pastes, among others. In these embodiments, pharmaceutical solvents for liquid dosage forms of oral transmucosal compositions include water, glycerin, propylene glycol, liquid polyethylene glycols of various molecular weights, ethyl oleate, medium chain triglycerides, isopropyl myristate, isopropyl palmitate, isopropyl stearate, other pharmaceutically acceptable esters of C8-C22 fatty acids and C2-C6 alcohols, mineral oil, and vegetable oils, among others. Further to these embodiments, C8-C22 fatty acids include fatty acids having from 8 to 22 carbon atoms, such as, for example myristic acid, palmitic acid, stearic acid, arachidic acid, or oleic acid, among others. Still further to these embodiments, C2-C6 alcohols include alcohols having from 2 to 6 carbon atoms, in particular the C2-C5 alcohols as well as the homologues with 6 carbon atoms including diols and triols, such as, for example ethanol, propylene glycol, and glycerol, among others. Examples of vegetable oils include almond oil, peanut oil, sesame oil, sunflower oil, safflower oil, canola oil, corn oil, and olive oil, among others.

In some embodiments, oral transmucosal ointments and pastes include petrolatum, PCCA Plasticized™ base, paraffin wax, various synthetic wax, lanolin, beeswax, carnauba wax, candelila wax, silicones, isopropylesters, polyols, cellulose ethers, among other suitable bases. In addition, ointment bases also include suitable pharmaceutical solvents, such as, for example water, liquid polyethylene glycols of various molecular weights, ethyl oleate, medium chain triglycerides, isopropyl myristate, isopropyl palmitate, isopropyl stearate, and other pharmaceutically acceptable esters of C8-C22 fatty acids and C2-C6 alcohols, mineral oil, and vegetable oils, among others.

Administration

In some embodiments, oral transmucosal compositions allow the delivery of testosterone and C-SERM directly into the patient's bloodstream bypassing the gastrointestinal tract and the hepatic metabolism. Bypassing the hepatic metabolism results in a higher percentage of bioavailability of the APIs to the patient, and also results in lower dosage requirements of testosterone.

In some embodiments, oral transmucosal compositions are administered in the oral cavity at the sublingual, palatal, buccal, gingival, or the like. Oral transmucosal compositions may be self-administered by the patient or administered by a medical practitioner, such as, a physician or nurse.

In some embodiments, oral transmucosal compositions include liquid dosage forms, such as, for example sublingual solutions, emulsions, suspensions, and liquid sprays, among others. In other embodiments, oral transmucosal compositions include solid dosage forms, such as, sublingual tablets and buccal troches, among others. In yet other embodiments, oral transmucosal dosage forms include chewing gums.

In some embodiments, oral transmucosal dosage forms include mucoadhesive polymers as part of the compositions. Examples of dosage forms having mucoadhesive polymers include mucoadhesive thin strips, thin films, tablets, patches, and tapes, among others. In other embodiments, dosage forms include: mucoadhesive liquids, such as, gel-forming liquids; semisolids, such as, for example gels, gel-forming ointments, and gel-forming pastes; gel-forming powders; or any other dosage forms that exhibit mucoadhesive properties and provide oral transmucosal delivery of APIs.

In some embodiments, oral transmucosal dosage forms are designed for fast release and transmucosal absorption of testosterone and C-SERMs. In other embodiments, oral transmucosal dosage forms are designed for slow release and absorption of testosterone and C-SERMs over a prolonged period of time.

In some embodiments, oral transmucosal compositions are administered in a single administration whereby a certain amount of testosterone and C-SERM are administered together. In an example, one puff of a spray solution is administered representing the full desired dose. In other embodiments, oral transmucosal compositions are administered by multiple administrations in one or more sub-doses over a specified period of time. In an example, one, two or more puffs of a smaller dose of the oral transmucosal composition are administered—preferably one after another in quick succession.

In some embodiments, oral transmucosal compositions may be tailored for individual patients according to clinical symptoms and baseline serum concentrations of testosterone and estradiol. In these embodiments, these oral transmucosal compositions may be prescribed with various concentrations of testosterone and C-SERM and suitable dosage regimens to more closely mimic the circadian rhythm and physiological pulsatile secretion of testosterone, thereby keeping the testosterone and estradiol levels within physiologic range.

In some embodiments, low dose APIs in any of the above identified dosage forms may result in acceptable testosterone levels in the patient. This contrasts with current popular topical treatment options, which use very high dosages of testosterone to get a few milligrams of testosterone absorbed into the bloodstream.

In some embodiments, the dosages (e.g., daily) required depend on the type of C-SERM included in the disclosed oral transmucosal compositions. In other words, some C-SERMs are more potent than others, and hence, the dosing can vary among the various C-SERMs used.

In an example, oral transmucosal compositions are administered within a dosage range from about 25 mg/day to about 100 mg/day of testosterone, preferably from about 25 mg/day to about 50 mg/day; and from about 5 mg/day to about 100 mg/day of clomiphene, preferably from about 25 mg/day to about 50 mg/day.

The following examples are intended to illustrate the scope of the disclosure and are not intended to be limiting. It is to be understood that other pharmaceutical formulations known to those skilled in the art may alternatively be used.

EXAMPLES

Exemplary dosage forms of the oral transmucosal compositions are described below.

Example #1 illustrates formula for one sublingual tablet:

| Ingredient | Composition |
|---|---|
| Clomiphene citrate | 12.5 mg |
| Testosterone | 12.5 mg |
| Penetration enhancer(s) | 1-10% |
| Flavor(s) | 0.5-5% |
| Lactose/sucrose (80:20) | q.s. 155-250 mg |

Example #2 illustrates formula for one dose of sublingual drops:

| Ingredient | Composition |
|---|---|
| Clomiphene citrate | 12.5 mg |
| Testosterone | 12.5 mg |
| Co-Solvents (Glycerin, Polysorbate 20) | 10-50% |
| Penetration enhancer (Dimethyl sulfoxide) | 1-10% |
| Flavor(s) | 0.5-5% |
| Sweetener(s) | 0.1-1.5% |
| Base Solvent (Ethanol) | q.s. 0.2 mL |

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A pharmaceutical composition, comprising a clomiphene-like selective estrogen receptor modulator (C-SERM), testosterone and at least one penetration enhancer, wherein the C-SERM and testosterone are present in equal amounts.

2. The pharmaceutical composition of claim 1, wherein the C-SERM is clomiphene citrate.

3. The pharmaceutical composition of claim 1, wherein the penetration enhancer is present at about 1% to about 20% of the composition.

4. The pharmaceutical composition of claim 1, wherein the penetration enhancer is present at about 1% to about 10% of the composition.

5. The pharmaceutical composition of claim 1, further comprising at least one sugar.

6. The pharmaceutical composition of claim 1, further comprising lactose and sucrose.

7. The pharmaceutical composition of claim 6, wherein the lactose and sucrose are present in a 80:20 ratio.

8. The pharmaceutical composition of claim 1, wherein the pharmaceutical composition is in tablet form.

9. The pharmaceutical composition of claim 1, wherein the penetration enhancer is dimethyl sulfoxide.

10. The pharmaceutical composition of claim 1, wherein the testosterone is an ester selected form the group consisting of testosterone cypionate, testosterone propionate, testosterone enanthate, testosterone heptylate, testosterone caproate, testosterone phenylpropionate, testosterone isocaproate, testosterone decanoate, testosterone acetate, testosterone laurate, or a pharmaceutically acceptable ester thereof, and combinations thereof.

* * * * *